United States Patent
Bynum et al.

(10) Patent No.: US 6,965,108 B2
(45) Date of Patent: Nov. 15, 2005

(54) METHOD AND APPARATUS FOR THREE DIMENSIONAL IMAGING USING INFRARED RADIATION

(75) Inventors: Kevin C. Bynum, Yonkers, NY (US); Abe S. Kassis, Yonkers, NY (US)

(73) Assignee: Euro-Celtique, S.A., Luxembourg (LU)

( * ) Notice: Subject to any disclaimer, the term of this patent is extended or adjusted under 35 U.S.C. 154(b) by 112 days.

(21) Appl. No.: 09/918,239

(22) Filed: Jul. 30, 2001

(65) Prior Publication Data

US 2004/0211903 A1 Oct. 28, 2004

(51) Int. Cl.$^7$ .............................................. G01N 21/35
(52) U.S. Cl. ................................................... 250/341.1
(58) Field of Search ....................................... 250/341.1

(56) References Cited

U.S. PATENT DOCUMENTS

| | | | |
|---|---|---|---|
| 5,068,882 A | 11/1991 | Eberhard | 378/4 |
| 5,073,910 A | 12/1991 | Eberhard et al. | 378/4 |
| 5,137,355 A | 8/1992 | Barbour et al. | 356/342 |
| 5,257,183 A | 10/1993 | Tam | 364/413.19 |
| 5,459,570 A | 10/1995 | Swanson et al. | 356/345 |
| 5,491,552 A | 2/1996 | Knuttel | 356/360 |
| 5,664,574 A | 9/1997 | Chance | 128/664 |
| 6,081,322 A | 6/2000 | Barbour | 356/73.1 |
| 6,088,100 A | 7/2000 | Brenan et al. | 356/346 |
| 6,345,194 B1 * | 2/2002 | Nelson et al. | 600/425 |

OTHER PUBLICATIONS

*Image Processing Toolbox*, ver. 2, Mathworks, Inc., Natick, MA, 1998, 6–19 to 6–32 and 11–154.

\* cited by examiner

*Primary Examiner*—Constantine Hannaher
(74) *Attorney, Agent, or Firm*—Davidson, Davidson & Kappel, LLC

(57) ABSTRACT

An infrared three-dimensional imaging system and method in which an object is irradiated by monochromatic radiation in the near-infrared or mid-infrared region of the spectrum. A spectral image is captured for each wavelength in a spectral range by a radiation detector to create a spectral image data block that is stored on a data storage device. The object is rotated by some predetermined angular increment until a complete three hundred and sixty degree view is obtained so that a spectral image data block is created for each angular position. Each spectral image data block is compressed to its most relevant spectral information and used to re-create a three dimensional image by a known computerized tomography algorithm.

90 Claims, 7 Drawing Sheets

METHOD AND APPARATUS FOR THREE DIMENSIONAL IMAGING USING INFRARED RADIATION

FIELD OF THE INVENTION

The present invention relates generally to three-dimensional (3D) tomography.

BACKGROUND OF THE INVENTION

Every type of atom and molecule vibrates at different speeds, giving off light at its own unique set of frequencies. Thus, the chemical composition of an object can be ascertained by studying light that passes through an object. This field of science is known as spectroscopy. The light, when projected on some medium after passing through an object, creates a spectral image. When applied in a two-dimensional world, this technique is known as 2D imaging, or hyper spectral imaging. When spectroscopy and imaging are applied through a three dimensional volume it is known as 3D tomography. This technique is utilized routinely in the medical field in the form of computerized tomography (CT), which uses x-rays to provide a nondestructive or noninvasive method of generating visual sectional views of an object.

In general, a computerized tomography (CT) apparatus performs three processes: scanning, image reconstruction and image display. X-rays are projected over an object positioned between an x-ray source and an x-ray detector. The x-ray source and detector, or object, are moved to scan the entire surface of the object. The detector measures how much of the x-rays penetrate the object to create penetration data that is converted into digital form and stored on a computer. The computer uses the digitized penetration data to create an image of the object by some conversion algorithm and displays the image on a monitor. The displayed image is a function of the density of the object.

In conventional computerized tomography, an x-ray beam in the shape of a fan, and a linear array detector are employed to achieve two-dimensional (2D) imaging. While the data set is complete and image quality is correspondingly high, only a single slice of an object is imaged at a time. When a 3D image is required, a "stack of slices" approach has been employed. Acquiring a 3D data set a 2D slice at a time is inherently tedious and time-consuming.

A more recent approach, based on what is called cone beam geometry, employs a two-dimensional array detector instead of a linear array detector, and a cone beam x-ray source instead of a fan beam x-ray source. At any instant, the entire object is irradiated by the cone beam x-ray source, making cone beam geometry much faster than slice-by-slice scanning using a fan beam or a parallel beam. Also, since each "point" in the object is viewed by the x-rays in 3D rather than in 2D, much higher contrast can be achieved than is possible with conventional 2D x-ray CT. To acquire cone beam projection data, an object is scanned, preferably over a 360-degree angular range, either by moving the x-ray source in an appropriate scanning trajectory, for example, a circular trajectory around the object, while keeping the 2D array detector fixed with reference to the source, or by rotating the object while the source and detector remain stationary. In either case, it is relative movement between the source and object that effects scanning.

Image reconstruction procedures in x-ray CT are often based on the Radon inversion process, in which the image of an object is reconstructed from the totality of the Radon transform of the object. The Radon transform of a 2D object comprises integrals of the object density on lines intersecting the object. The Radon transform of a 3D object comprises planar integrals. The cone beam data, however, are not directly compatible with image reconstruction through inverse Radon transformation, which requires the use of planar integrals of the object as input. Consequently, image reconstruction by inversion from cone beam scanning data generally comprises two steps: (1) convert the cone beam data to planar integrals, and (2) perform an inverse Radon transform on the planar integrals to obtain the image.

Infrared spectroscopy is a technique which is based upon the vibrational changes of the atoms of a molecule. In accordance with infrared spectroscopy, an infrared spectrum is generated by transmitting infrared radiation through a sample of an organic compound and determining what portion of the incident radiation are absorbed by the sample. An infrared spectrum is a plot of absorbance (or transmittance) against wavenumber, wavelength, or frequency. Infrared radiation is radiation having a wavelength between about 750 nm and about 1000 $\mu$m. Near-infrared radiation is radiation having a wavelength between about 750 nm and about 2500 nm. Mid-infrared radiation is radiation having a wavelength between about 2500 nm and about 10,000 nm.

A variety of different types of spectrometers are known in the art such as grating spectrometers, FT (Fourier transformation) spectrometers, Hadamard transformation spectrometers, AOTF (Acousto Optical Tunable Filter) spectrometers, diode array spectrometers, filter-type spectrometers, scanning dispersive spectrometers and nondispersive spectrometers.

Filter-type spectrometers, for example, utilize an inert solid heated to provide continuous radiation (e.g. tungsten filament lamp) to illuminate a rotating opaque disk, wherein the disk includes a number of narrow bandpass optical filters. The disk is then rotated so that each of the narrow bandpass filters passes between the light source and the sample. An encoder indicates which optical filter is presently under the light source. The filters filter the light from the light source so that only a narrow selected wavelength range passes through the filter to the sample. Optical detectors are positioned to detect light which either is reflected by the sample (to obtain a reflectance spectra) or is transmitted through the sample (to generate a transmittance spectra). The amount of detected light is then measured, which provides an indication of the amount of absorbance of the light by the substance under analysis.

An LED Illumination Array can use infrared emitting diodes (IREDs) as sources of near infrared radiation. A plurality (for example, eight) of IREDs are arranged over a sample work surface to be illuminated for quantitative analysis. Near-infrared radiation emitted from each IRED impinges upon an accompanying optical filter. Each optical filter is a narrow bandpass filter which passes NIR radiation at a different wavelength. NIR radiation passing through the sample is detected by a detector (such as a silicon photodetector). The amount of detected light is then measured, which provides an indication of the amount of absorbance of the light by the substance under analysis.

Acousto Optical Tunable Filter spectrometers utilize an RF signal to generate acoustic waves in a $TeO_2$ crystal. A light source transmits a beam of light through the crystal, and the interaction between the crystal and the RF signal splits the beam of light into three beams: a center beam of unaltered white light and two beams of monochromatic and orthogonally polarized light. A sample is placed in the path of one of the monochromatic beam detectors, which are positioned to detect light which either is reflected by the sample (to obtain a reflectance spectra) or is transmitted through the sample (to generate a transmittance spectra). The wavelength of the light source is incremented across a wavelength band of interest by varying the RF frequency. The amount of detected light is then measured, which provides an indication of the amount of absorbance of the light by the substance under analysis.

In grating monochromator spectrometers, a light source transmits a beam of light through an entrance slit and onto a diffraction grating (the dispersive element) to disperse the light beam into a plurality of beams of different wavelengths (i.e., a dispersed spectrum). The dispersed light is then reflected back through an exit slit onto a detector. By selectively altering the path of the dispersed spectrum relative to the exit slit, the wavelength of the light directed to the detector can be varied. The amount of detected light is then measured, which provides an indication of the amount of absorbance of the light by the substance under analysis. The width of the entrance and exit slits can be varied to compensate for any variation of the source energy with wavenumber.

Detectors used in spectroscopy generally fall into two classes, photographic detectors, in which radiation impinges upon an unexposed photographic film, and electronic detectors, in which the radiation impinges upon a detector and is converted into an electrical signal. Electronic detectors provide the advantage of increased speed and accuracy, as well as the ability to convert the spectral data into an electronic format, which can be displayed, processed, and/or stored. Examples of electronic detectors include photomultiplier tubes and photodetectors. Photomultiplier tubes are quite sensitive, but are relatively large and expensive. Photodetectors provide the advantage of reduced size and cost. Some examples of photodetectors are pin diode detectors, charge coupled device detectors, and charge injection device detectors.

SUMMARY OF THE INVENTION

Two distinctly different approaches to material characterization, spectroscopy and imaging, when combined, can provide spatial chemical information of an object (the chemical composition at specific points in an object).

The present invention provides a three-dimensional spectral imaging system for obtaining image information of an object. A source of collimated radiation disposed at a proximal side of the object passes a radiation beam having a predetermined wavelength through the object at a scanning angle. The source of collimated radiation may, for example, be comprises of a radiation source and a beam collimator, wherein the beam collimator is disposed between the radiation source and the object. A scanning angle changer is operatively connected to at least one of the radiation source and the object. A radiation detector disposed at a distal side of the object detects a plurality of two-dimensional spectral images of the object. A control computer effects operation of the radiation source, the radiation detector, and the scanning position changer, to capture the plurality of two-dimensional spectral images. The control computer also determines a three-dimensional image of the object using the plurality of two-dimensional spectral images. The imaging system may further include an image display device for displaying the three-dimensional image.

The beam collimator may be a focusing lens, and the system may also include a first set of optical elements disposed between the focusing lens and the object and a second set of optical elements disposed between the object and the radiation detector. The first and second set of optical elements may include, for example, a polarizer and a quarter-wave plate. The control computer may include a data storage device for storing the plurality of two-dimensional spectral images. The radiation source may includes a lamp and a monochrometer and the radiation beam may be a near infrared radiation beam, a mid-infrared radiation beam, or a radiation beam having some other wavelength range. The radiation source may include a wavelength filter for causing the radiation beam to have the predetermined wavelength. The scanning angle changer changes the scanning angle by changing a relative position of the object or radiation source. It may rotate the object, for example on a rotating stage, it may change the position of the radiation source relative to the object, or it may operate individually a plurality of radiation sources disposed in a circular relationship relative to the object to change a respective scanning angle between each of the plurality of radiation sources and the object.

The radiation detector may be a CCD detector, such as an indium antimony liquid nitrogen cooled focal plane array camera, or other focal plane array camera. Software written in a MATLAB® programming language may be executed by the control computer to perform the determining of the three-dimensional image. The control computer may effect the system components to change the predetermined wavelength of the radiation beam and the scanning angle change so that each of the plurality of two-dimensional spectral images has a respective scanning angle and a respective wavelength. The control computer may determine a spectral image data block by capturing a plurality two-dimensional spectral images at a same respective predetermined scanning angle and a different respective predetermined wavelength. Preferably, the control computer captures two-dimensional spectral images at a plurality of respective predetermined scanning angles so as to provide a 360 degree view of the object and so as to determine a plurality of respective spectral image data blocks, which the control computer preferably compresses to their most relevant information. The control computer may then generate a respective RGB false color image from each of the plurality of respective spectral image data blocks. The control computer may then combine the RGB false color images to create a three-dimensional volume visualization package, which the control computer uses to determine the three-dimensional image.

Examples of objects that can be advatageously imaged according to the present invention include a solid pharmaceutical dose, a microsphere, (preferably encapsulated by an appropriate material), a biological tissue, or a transdermal patch.

The present invention also provides a method for three-dimensional imaging of an object. According to the method, a radiation beam having a predetermined wavelength is directed from a radiation source through the object at a predetermined scanning angle. The radiation beam is collimated before hitting the object. The predetermined wavelength and predetermined scanning angle are changed in order to capture a plurality of two-dimensional spectral images of the object, each of the plurality of two-dimensional spectral images being captured at a respective scanning angle and a respective predetermined wavelength. A three-dimensional image of the object using the plurality of two-dimensional spectral images is then reconstructed.

The three-dimensional image may then be displayed on an image display device.

A further system for three-dimensional imaging is provided whereby near-infrared radiation (NIR) is used to obtain the spectral image of an object. The system comprises a near infrared radiation source, a focusing lens, two sets of a polarizer and a quarter-wave plate, a scanning angle changer, a radiation detector, a data storage device, and a control computer. The computer is operatively connected to the radiation source, the radiation detector and the scanning angle changer for control of their operation by a software object residing on the control computer. The software object is executable by the computer to effect operation of system components in a prescribed sequence to obtain image reconstruction data by capturing a spectral image of an object irradiated by the near infrared radiation source and to reconstruct a three-dimensional image of the object.

A monochromatic beam of light is projected through a combination of lens elements, namely the focusing lens and the first polarizer and quarter-wave plate, to irradiate an object. Light transmitted through the object without any phase change, passes through a second polarizer and quarter-wave plate and onto a charge couple detector (CCD) for capturing the spectral image of the sample. The process is repeated for each wavelength of a desired spectral range to create a spectral data block.

The relative scanning angle (relation of the scanning elements to the object) is then changed to effect scanning from a different angle and another spectral data block is obtained. The scanning angle is changed at predetermined angular increments until a complete 360 degree view is obtained for the desired spectral range at each angular incremental position.

Each spectral data block is compressed to its most relevant spectral information to generate a false color image of the scanned object at each angular position. The false color images are combined to create a final 3D data volume using a known computerized tomography algorithm.

The present invention also provides a method including irradiating an object with near infrared radiation at a predetermined wavelength to capture the spectral image of an object and store the image on a data storage device. The predetermined wavelength is changed and another spectral image captured and stored. This is repeated for each wavelength in a spectral range to create a spectral image data block. The method also comprises changing the position of the object in relation to the near infrared radiation source and obtaining another spectral image data block at the new position until a full 360 degree view is obtained, compressing each of the spectral data blocks to its most relevant spectral information, generating a number of images from each of the compressed spectral data blocks, generating an RGB false color image from the number of images corresponding for each scanning angle, combining the RGB images to create a final three-dimensional data volume using a computerized tomography algorithm, and displaying a final three-dimensional image using a three-dimensional volume visualization package.

Preferably, the system can acquire two-dimensional spectral images at least throughout the near infrared and mid infrared spectra.

DETAILED DESCRIPTION OF THE PREFERRED EMBODIMENTS

Figure 1:
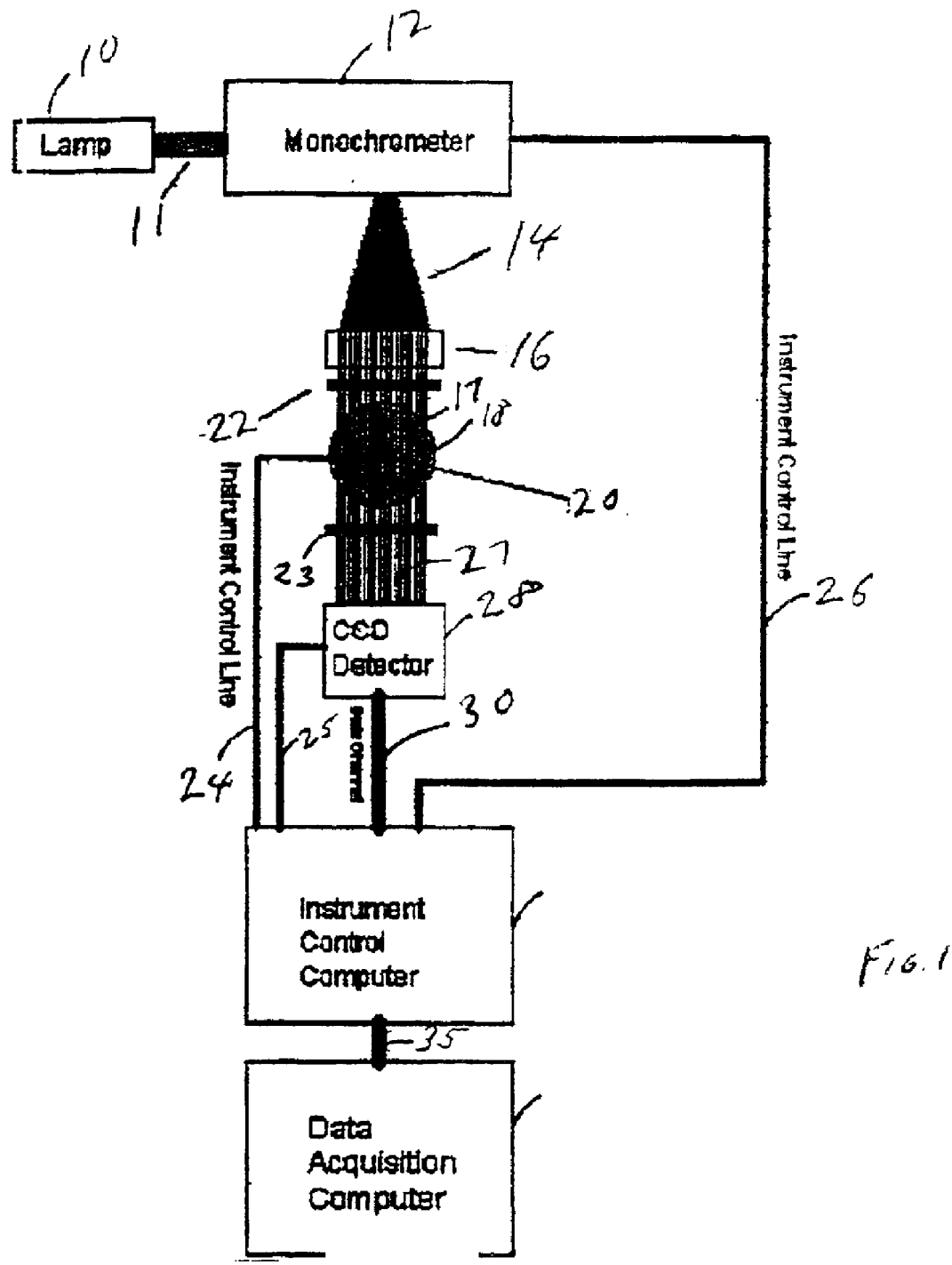
FIG. 1 is a block diagram of a three dimensional NIR imaging system according to the present invention.

Referring to FIG. 1, there is shown an exemplary infrared tomography system according to the present invention. Preferably, the system is automated by a computer program residing on the control computer 32 operably connected to each component in the system by instrument control lines 24, 25 and 26. The control lines 24, 25 and 26 are constructed and arranged to allow for the exchange of digital information between the computer 32 and the system components to effect operation in a prescribed sequence at the direction of the program, and to transfer digital imaging information to the control computer 32 for storage on the data acquisition computer 34.

A lamp 10 provides a beam of light 11 to a monochrometer 12, which, in turn, projects monochromatic (one wavelength) radiation 14. As already discussed, a wide variety of monochrometers are suitable for generating the monochromatic radiation, including, for example, dispersive-type monochrometers and filter-type monochrometers. Moreover, the lamp 10 and monochrometer 12 could be replaced with a monochromatic light source such as an LED array.

The predetermined wavelength of the radiation 14 is selected from a spectral range which is generally selected based upon the composition of the object being scanned. The spectral range is a predetermined range of wavelengths within which scanning is performed to analyze an object to determine its chemical composition. For example, assume it is desired to determine the chemical spatial information of a tablet known to be composed of acetaminophen, codeine and caffeine. Assume further that it is known that the molecular structure of acetometaphin vibrates at a frequency allowing light with a wavelength of 1000 nanometers to pass, that codeine will allow light at 1150 nanometers to pass and that caffeine will allow light at 1200 nanometers to pass. It should be noted that these figures are totally arbitrary and chosen for their simplicity. The spectral range, therefore, would be between 1000 and 1200 nanometers because it is known that there are only three elements in the tablet and their vibrating frequencies correspond to light having wavelengths between 1000 and 1200 nanometers. Therefore, there should be no need to scan the object with light having a wavelength below 1000 nanometers or above 1200 nanometers.

Once each of the predetermined wavelengths are known (or have been thus determined), each of the predetermined wavelengths of radiation 14 in the spectral range be stepped though, skipping any values in between. Preferably, the system starts with one of the predetermined wavelengths (i.e. 1000 nanometers) and scanning is sequentially performed at each of the other predetermined wavelength in the spectral range (i.e. 1150 and 1200 nanometers). A set of LEDs may advantageously be used as a radiation source to generate the correct monochromatic wavelengths, once the predetermined wavelengths are known.

The monochromatic radiation is projected, preferably, in a cone beam 14 through a beam collimator 16 (for example, a focusing lens 16) and through a first set of optical elements 22. Advantageously, the first set of optical elements can include a polarizer to circularly polarize the radiation, and quarter-wave plate to introduce a phase difference of one-quarter cycle between the ordinary and extraordinary components of radiation passing through. The circularly polarized, phase-shifted, collimated radiation beam 17 radiates the object 20 (in this example a tablet), positioned on a rotating stage 18. The cross-sectional area of the collimated radiation beam 17 should be at least large enough to cover the area of interest of the object, and preferably large enough to cover the entire object at each scanning angle. The stage 18 rotates (after the object has been scanned at each of the predetermined wavelengths in the spectral range) to effect scanning at different scanning angles in order to obtain a complete 360 degree view of the object.

While this architecture is preferred, other methods and apparatuses can be used to change the relative scanning angle. For example, the object may be stationary and the scanning apparatus moved in a circular trajectory around the sample. Alternatively, a plurality of monochromters disposed in a circular trajectory may be employed with one detector so that using one monochrometer at a time, in succession, changes the relative scanning angle of the object.

After passing through the object, any radiation that has not been scattered or absorbed by the object passes through a second set of optical elements 23. In the exemplary embodiment of FIG. 1 the second set of optical elements also includes a circular polarizer and quarter-wave plate.

Figure 2:
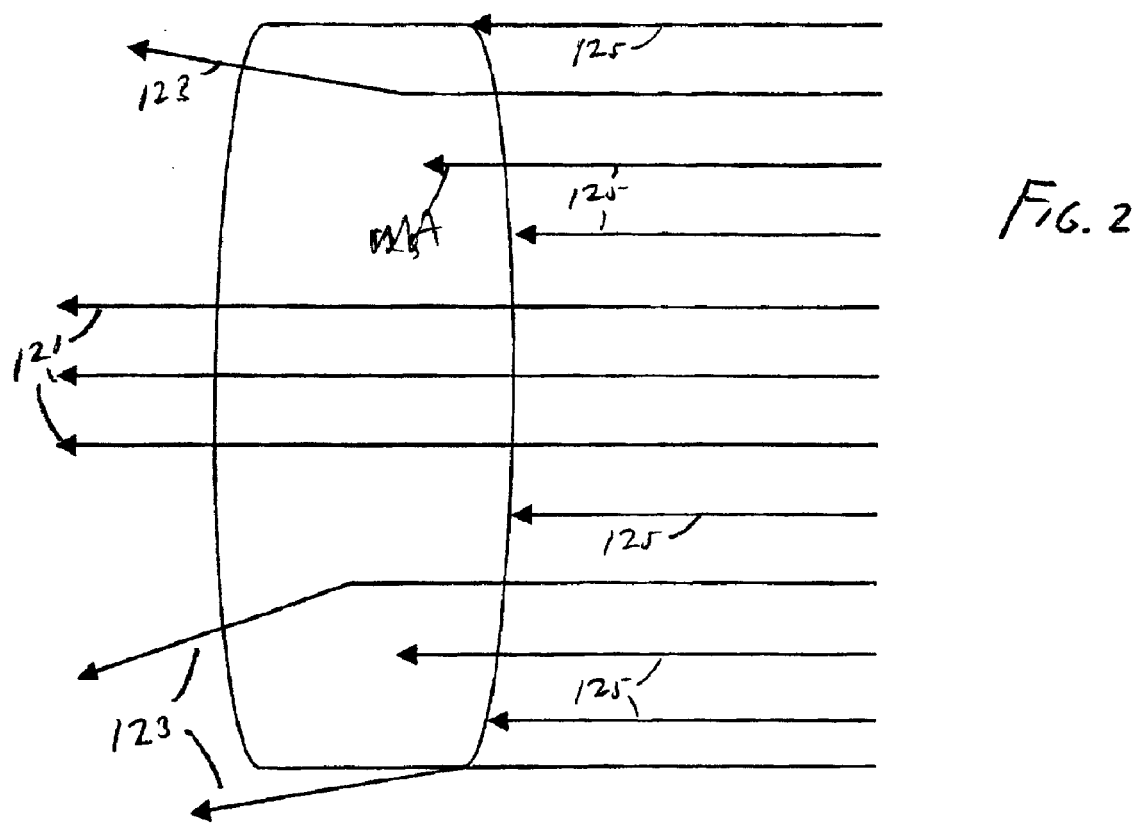
FIG. 2 depicts monochromatic radiation being absorbed, scattered and passed through a tablet scanned by the system of FIG. 1.

Referring to FIG. 2, when the radiation 17 at 100 nanometers strikes the tablet 20, some will be absorbed 125, some will be transferred through the tablet 121, and some will scatter 123. As previously mentioned, the atoms in the tablet 20 vibrate at a particular frequency. The radiation 121 will pass through the tablet 20 where its chemical composition contains molecules vibrating at the frequency required to let the light 17 pass. Therefore, the light 17 will pass through the tablet 20 only where there is acetometaphin so that the position of the light striking the CCD detector indicates the position of the acetometaphin in the sample on a two-dimensional plane. Scattered radiation 123 will have its polarization angle and/or phase altered, preventing it from passing through the second quarter-wave plate and polarizer 23 and striking the CCD detector 28. The light transmitted through the tablet 20 without a change in its polarization or phase angle will also pass through the second polarizer and quarter-wave plate 23 and radiate the charge couple device (CCD) detector 28, thereby producing a spectral image. The resulting spectral image will show where, and in what concentration, a certain compound is located in a two-dimensional plane representing the cross section of the tablet 20 projected onto the CCD detector 28. In general, the type of detector used will be dependent upon the wavelength region of the light 17. For near IR applications, the CCD detector may comprise a focal plane array camera. An exemplary near IR detector is a 256×256 InSb (indium antimony) liquid nitrogen cooled focal plane array camera is used. The intensity image of the transmitted light is stored on the data acquisition computer 34. The original image can be thought of as a cross section through the specimen, in which intensity values represent the density of the analyte.

Figure 3:
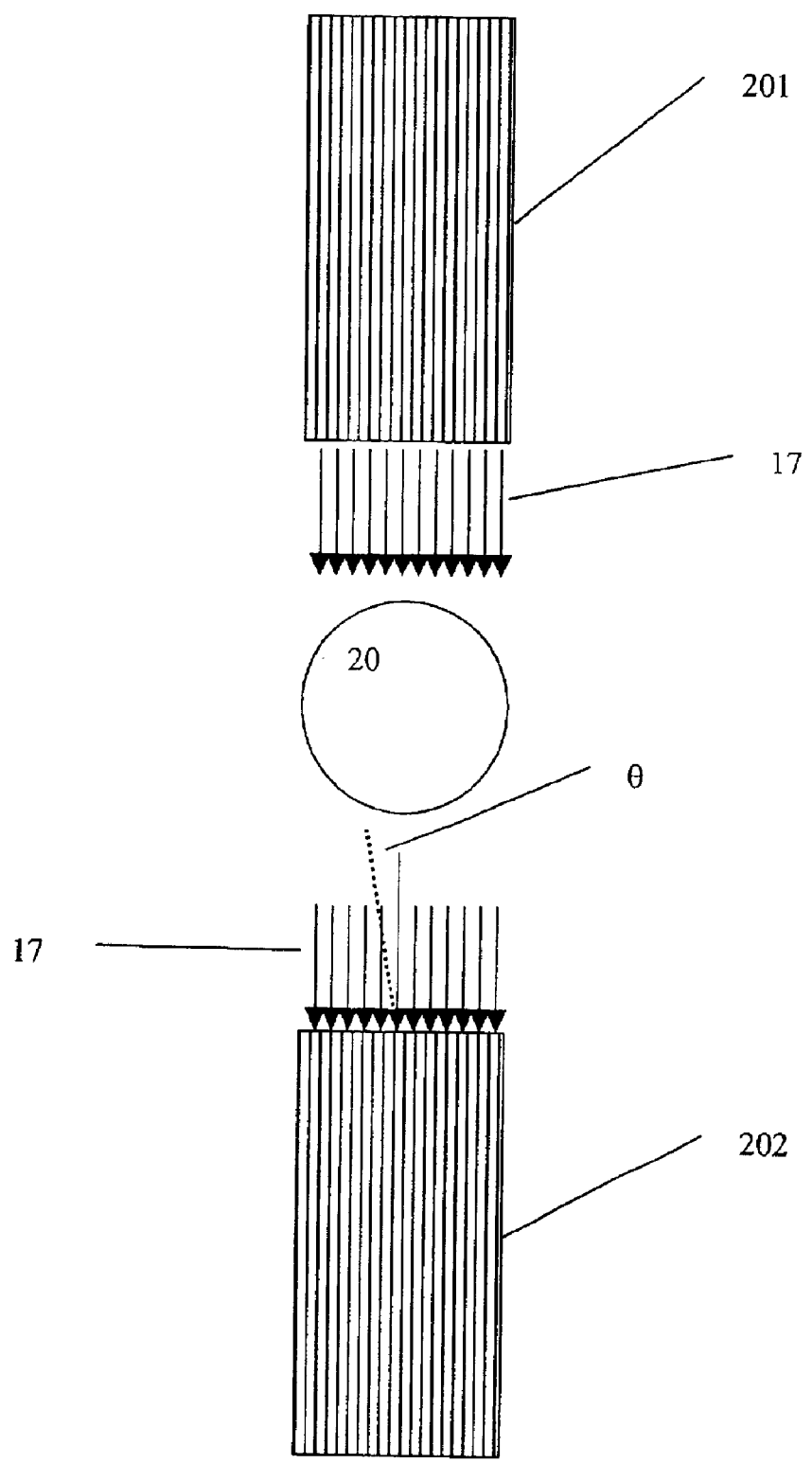
FIG. 3 depicts two corresponding arrays of optical fibers disposed as a transmitter and detector.

Alternative arrangements exist for collimating for collimating and detecting the radiation beam to ensure that only the radiation that has passed though the object without being scattered by the object is detected. According to one example shown in FIG. 3, the radiation 17 is transmitted through a dense an array of optical fibers 201 and detected by an identically corresponding array of optical fibers 202 disposed at the other side of the object 20. The fibers may be identically aligned such that there is a one-to-one correspondence between each fiber of the transmitting fiber array and each fiber of the detecting fiber array. The arrays can be aligned by passing radiation through the two fiber arrays without an object between them and adjusting their relative positions until maximum detection intensity is reached. The fibers in the detecting fiber array should be selected so as to have a limited acceptance angle $\theta$, for example between 0.5° and 5°. Thus, a detecting fiber having an acceptance angle $\theta$ of 0.5° would accept radiation which strikes it at an angle of less than 0.5° from the axis of the fiber, but would not accept radiation which strikes it at an angle greater than 0.5° from its axis.

Figure 4:
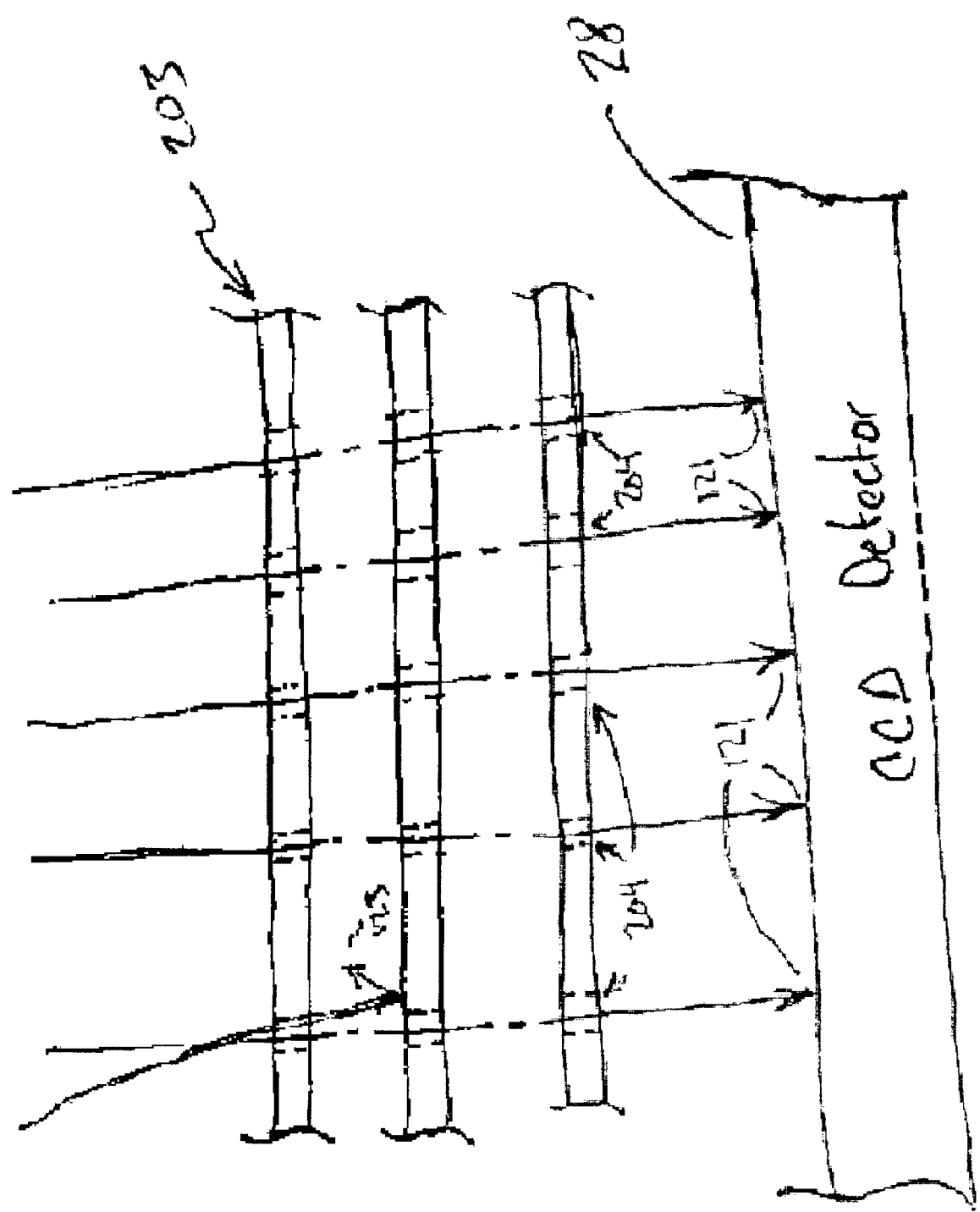
FIG. 4 depicts radiation passing through baffles in the form of a set of stacked plates each having an identical array of holes.

According to another example, a set of baffles can be used to only allow radiation having a particular propagation direction to pass through. For example, as shown in FIG. 4, a set of thin plates 203 could be used as baffles, each plate having an identical array of holes 204, the plates spaced apart from one another and the arrays of holes lined up with one another. Radiation 123 hitting the plates at a substantial angle with the axes of the aligned holes might pass through a hole in one or several plates, but eventually will hit the edge of the hole and be prevented from passing through the plates. Only radiation 121 having a propagation direction substantially parallel to the axes of the holes would be able to pass through the baffles and reach the detector 28. Such a set of baffles may be used on the transmitting end, near the radiation source, to collimate the beam. The baffles may also be used on the receiving end, in front of the radiation detector as shown in FIG. 4, to block scattered radiation and to make sure that only radiation having a propagation direction parallel to the axes of the holes (and therefore parallel to the propagation direction of the collimated beam before being passed through the object) can reach the radiation detector.

After obtaining the spectral image, the monochrometer 12 is stepped to the next predetermined wavelength in the spectral range, 115 nanometers in this case. The above steps are repeated until the desired spectral range is scanned to obtain a spectral image data block. The spectral image data block is a three-dimensional data set in the sense that the image is present in the x and y dimensions and the spectral data is located along the z dimension.

The rotating stage 18 turns a certain predetermined angular increment to a new position. The tablet 20 is imaged at each wavelength of the spectral range, creating a second data "block" at the new angular position. The tablet 20 is rotated through a full 360 degrees, stopping at each designated angular increment to create a spectral image block at each angular position, assuming ten degrees, the tablet is imaged at 10°, 20°, 30°, 40°, and so on up to 360°. The final outcome is a set of spectral image blocks representing the tablet 20 at each angular increment for each wavelength in the predetermined spectral range.

Each spectral data block is then compressed to its most relevant spectral information by some data reduction tool, such as Principal Component Analysis, to create a three-dimensional data set. As one of ordinary skill in the art will appreciate, the term Principal Component Analysis refers is a generic term which encompasses a number of well know data reduction tools, such as partial least squares, principal component regression, and multiple linear regression analysis, which may be used alone or in combination to identify one or more principal components in an analyte. As the use of Principal Component Analysis to analyze spectral data is well known in the art, it will not be discussed in detail herein. In any event a software object coded in a high level programming tool is preferably used for the data transformation to break down the three-dimensional data set into three images, each containing the data resulting from the three most significant principal components. The three images resulting from principal components 1, 2 and 3 respectively, can then be used to generate an RGB false color image for the final three dimensional image reconstruction. Although a data reduction tool such as principal component analysis is preferably used, in cases in which there is a sufficient difference between the spectral data at each wavelength, a simpler algorithm could be used. For example, if the absorbance ranged between 10 and 15 at a wavelength correspondence to caffeine, and the absorbance ranged between 100 and 125 for a wavelength corresponding to acetaminophen, At this point, the system has a single false color image of the sample at each angular position. These images are combined to create a final 3D data volume using a known computerized tomography algorithm, such as the Inverse Radon transform algorithm. The final 3D data set is viewed using a commercially available 3D-volume visualization package to allow for viewing still frames and animations of various layers in the 3D dataset.

The embodiment in FIG. 1 was described above as scanning a tablet 20 using near infrared radiation. The same system may also be used to scan other objects, including for example, other dosage forms such as capsules, transdermal patches, liquids, etc.

In addition, extremely small objects, including pharmaceutical compounds in the form of microparticles, microspheres and microcapsules may also be advantageously scanned using the system of FIG. 1. In scanning an object as small as a microsphere, infrared radiation having wavelengths in the range of 2500 to 5000 (i.e. mid-infrared radiation) is preferably used. Near infrared radiation as preferable when the object being scanned is relatively thick, since the shorter wavelengths may more easily penetrate the object. However near infrared radiation scans produce a less distinctive spectral image because of the relatively higher noise they produce. By comparison, microspheres are very thin and relatively transparent. Therefore, the longer wavelengths in the mid-infrared spectrum are preferable since they can penetrate the microspheres and generate less noise, thereby providing a more distinctive image.

Figure 5:
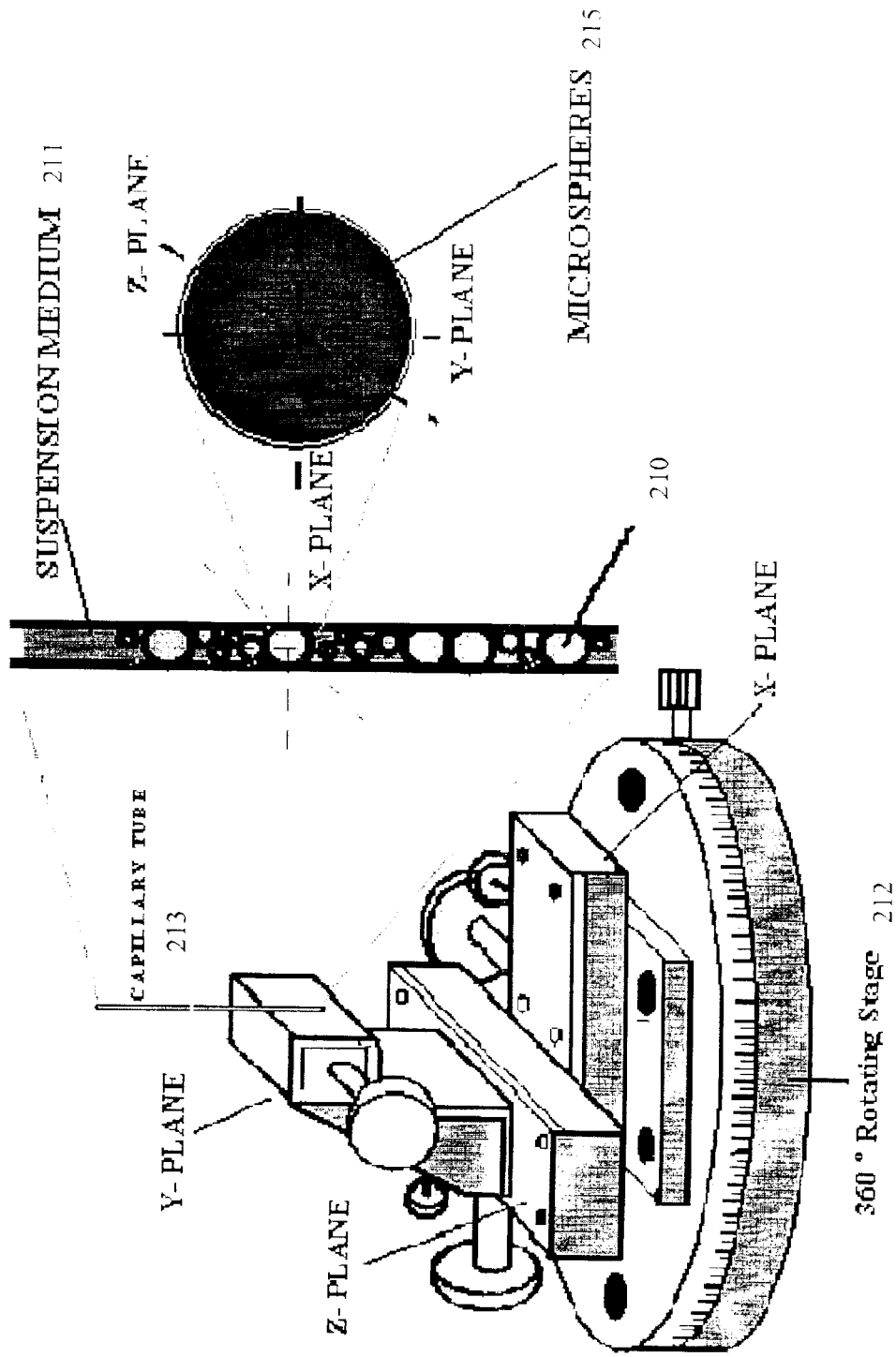
FIG. 5 depicts a detailed schematic of a microsphere being scanned according to the present invention.

In addition to being very small, microspheres are also relatively fragile. As shown in FIG. 5, to improve handling of a microsphere sample 210 during scanning, the microsphere sample 210 may be encapsulated in a suspension medium 211 which is transparent in the range of measurement. Examples of a suitable suspension medium include optical cement and silicon stop cock grease such as Nugol. The microsphere sample 210 in the suspension medium 211 may be advantageously placed in a capillary tube 213, which is then mounted onto the rotating stage 212. The position of the capillary tube 213 may be adjusted in the x-, y-, and z-plane, so that the beam of radiation is directed upon the microsphere 215. After the microsphere has been scanned at each of the relevant wavelengths in the range, the rotating stage changes the scanning angle and the microsphere 215 is scanned again. The procedure is repeated, as described above, until the microsphere 215 has been scanned at each of the relevant wavelengths over a 360 degree scanning angle range.

The data transformation, Radon transformation and image reconstruction are preferably done by a software program coded in a technical computing environment that provides core mathematics and advanced graphical tools for data analysis, visualization, and algorithm and application development, such as the MATLAB® numeric computing environment available from The Math Works, Inc. While such tools are preferred, it should be appreciated that alternative programming languages and environments, including, for example, Java, C, and C++ could alternatively be used. In this discussion that follows, however, the system of FIG. 1 will described in the context of a MATLAB® environment.

MATLAB® includes collections of products designed to address specific engineering and science tasks, known as product suites. The product suites include highly-optimized and application-specific functions built in the MATLAB® language called toolboxes.

A Data Acquisition Suite is provided to handle data acquisition and analysis process. The toolbox in the Data Acquisition Suite can import live, measured data directly into MATLAB® from external hardware. Referring back to FIG. 1, the program residing on the control computer 32 uses the Data Acquisition Toolbox to import measured data from the CCD detector 28 via the data channel 30, and from the data acquisition computer 34 via a connection 35.

An Image Processing Suite is provided to perform image processing and analysis. The toolbox for the Image Processing Suite includes the algorithm for the Radon image transformation, in a function that computes projections of an image matrix along specified directions. A projection of a two-dimensional function $f(x,y)$ is a line integral in a certain direction.

The toolbox also includes the function iradon. Iradon uses an inverse Radon transform to reconstruct images from projection data by performing the inverse Radon transform to invert a Radon transform and construct images from projection data. Given an image I and a set of angles theta, the function radon can be used to calculate the Radon transform with the command R=radon(I,theta). The function iradon can then be called to reconstruct the image I with the command line IR=iradon (R, theta).

Figure 6:
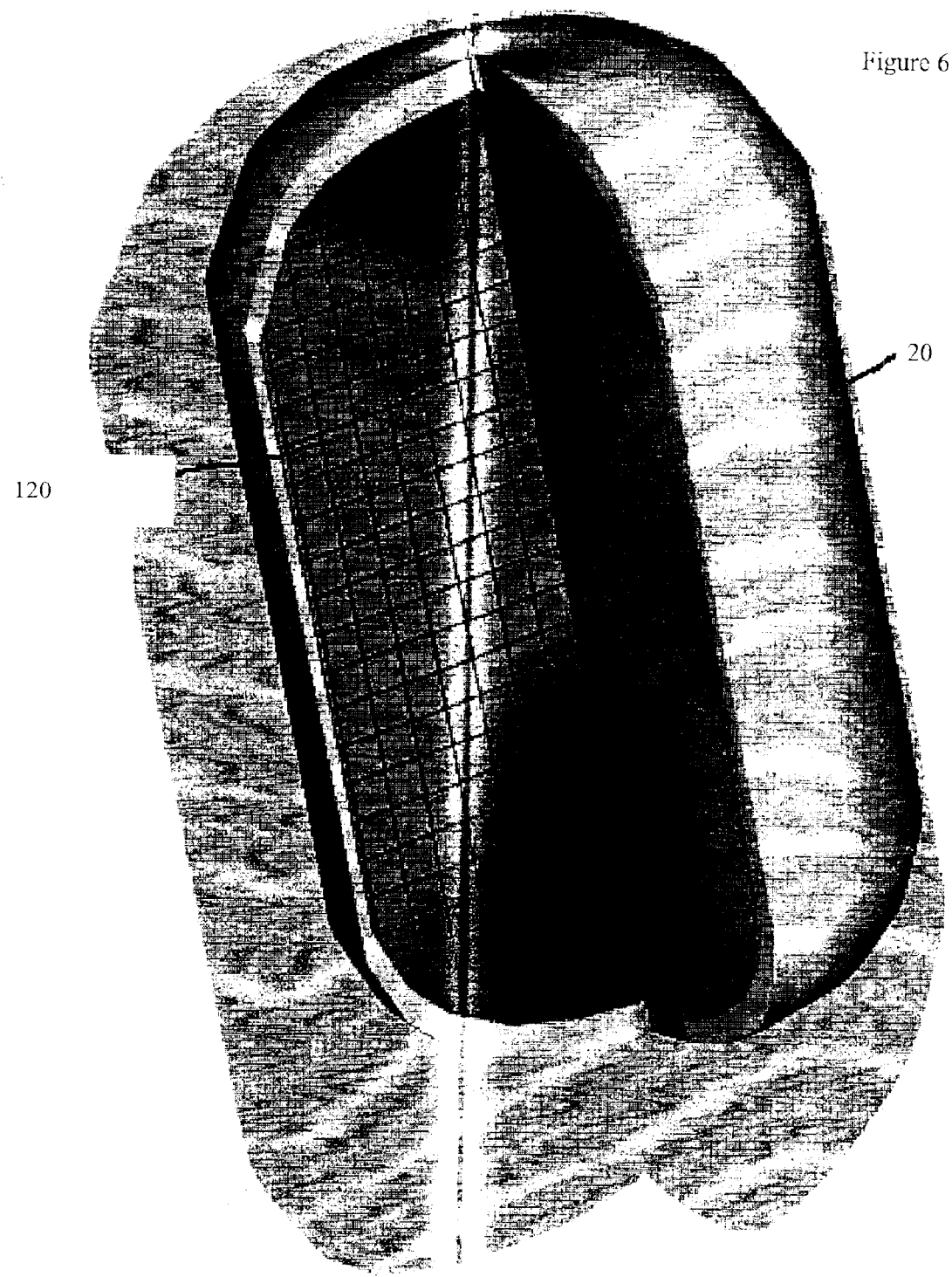
FIG. 6 illustrates an example of a three-dimensional display of an object.

As the use of the iradon transform for tomography applications is known in the art, it will not be discussed in detail herein. However, referring to FIG. 1, the projections (R) for the iradon transform are generated by measuring the attenuation of radiation that passes through the sample 20 at different angles. In this regard, the projections can be thought of as a cross section through the sample 20, in which intensity values represent the amount of an analyte found in the cross-section. These projections are generated by applying a data reduction tool (such as principal component analysis) to the spectral data recorded by the CCD Detector 28 to generate a two dimensional image that illustrates the presence of the analyte in the sample. In this regard, we note that the CCD detector comprises an array of detectors (e.g. a 320×240 array). An example of such a projection is shown in FIG. 6. The iradon transform then constructs a three dimensional image from the projections.

Filters can be used with the iradon transform to remove noise. Examples of such filters are hamming filters, Ram-Lak filters, Harm filters, Shep-Logan filters, Cosine filters. For example, the following call to iradon applies a Hamming window to the filter: IR=iradon(R,theta, 'Hamming').

In any event, the resulting image from the filtered back-projection algorithm will display the 3D volume of the object and its chemical composition throughout.

For a complete understanding of MATLAB® language and commands, the MATLAB® User's Guide is incorporated by reference in its entirety.

Referring to Table 1 below, there is shown an exemplary MATLAB® source code (MATLAB® 5.3) residing on the control computer to generate the three-dimensional model. This source code takes as input an array A(:,:,:,1) though A(:,:,:,36) which contains the two dimensional spectral data from the CCD detector 28 at 36 angular positions.

TABLE 1

| Line Ref. | Code |
|---|---|
| 1 | A = double(A); |
| 2 | THETA = [0:10:350]; |
| 3 | tomo = zeros (112, 112, 120); |
| 4 | PR = zeros (160, 36); |
| 5 | h = waitbar (0, 'Time Remaining') |
| 6 | % increment row slices |
| 7 | for i = 1:120; |
| 8 | for j = 1:36; |
| 9 | temp = A(i,:j); |
| 10 | temp = temp''; |
| 11 | PR(:,j) = temp; |
| 12 | waitbar ((i*j)/4320); |
| 13 | end |
| 14 | BPI = iradon (PR, THETA, 'linear', 'Hamming'); |
| 15 | %BPI= iradon (PR, THETA, 'linear', 'Ram-Lak'); |
| 16 | %BPI=iradon (PR, THETA, 'linear', 'Hann'); |
| 17 | %BPI=iradon (PR, THETA, 'linear,'Shepp-Logan'); |
| 18 | %BPI=iradon (PR, THETA, 'linear,'Cosine'); |
| 19 | tomo(:,:,i)=BPI; |
| 20 | end |
| 21 | close (h) |

The routine begins by defining an array of 36 angular positions in 10 degree increments (line 2). At line line 3, the routine sets up the variable to hold 120 iradon slices that are the result of the iradon transform. Lines 7 and 8 set up a loop for 120 slices, with a nested loop for the 36 images for each slice. In line 9, A(i:j) will contain the 36 two-dimensional images. For example, A(1:1) will contain two-dimensional images at 0 degrees. In line 11, the two dimensional image of image "j" is loaded. At line 13, the routine moves to the next j (i.e., next 10 degree increment). When the loop is complete, images of slice i at each of the 36 scanning angles have been loaded into the image array PR. In line 14, PR is the image array of 36 two-dimensional images, THETA is the angle (0–350 in 10-degree increments), "linear" is the interpolation method, and "Hamming" is the filter used. In lines 16–18, BPI is defined using other types of filters that might also be used, but these lines have been commented out. Line 19 defines a variable for holding the three-dimensional data for slice i. At line 20, the routine moves to the next slice i.

At the end of the routine shown in Table 1, an array tomo(x, z, i) is produced, where i is the slice, x is the x-ordinate, and z is the z-ordinate, wherein x ranges from 1–112, z ranges from 1–112, and i ranges form 1–120, giving an array with 1,505,280 voxels (or "volumetric pixels"). To display this image, any one of a variety of commercially available 3-D image display programs, for example, the Slicer Dicer program from Visual Logic, can be used. FIG. 6 depicts an example of a three-dimensional view of an object 20 reconstructed according to an array of voxels 120 produced by the above routine.

Figure 7:
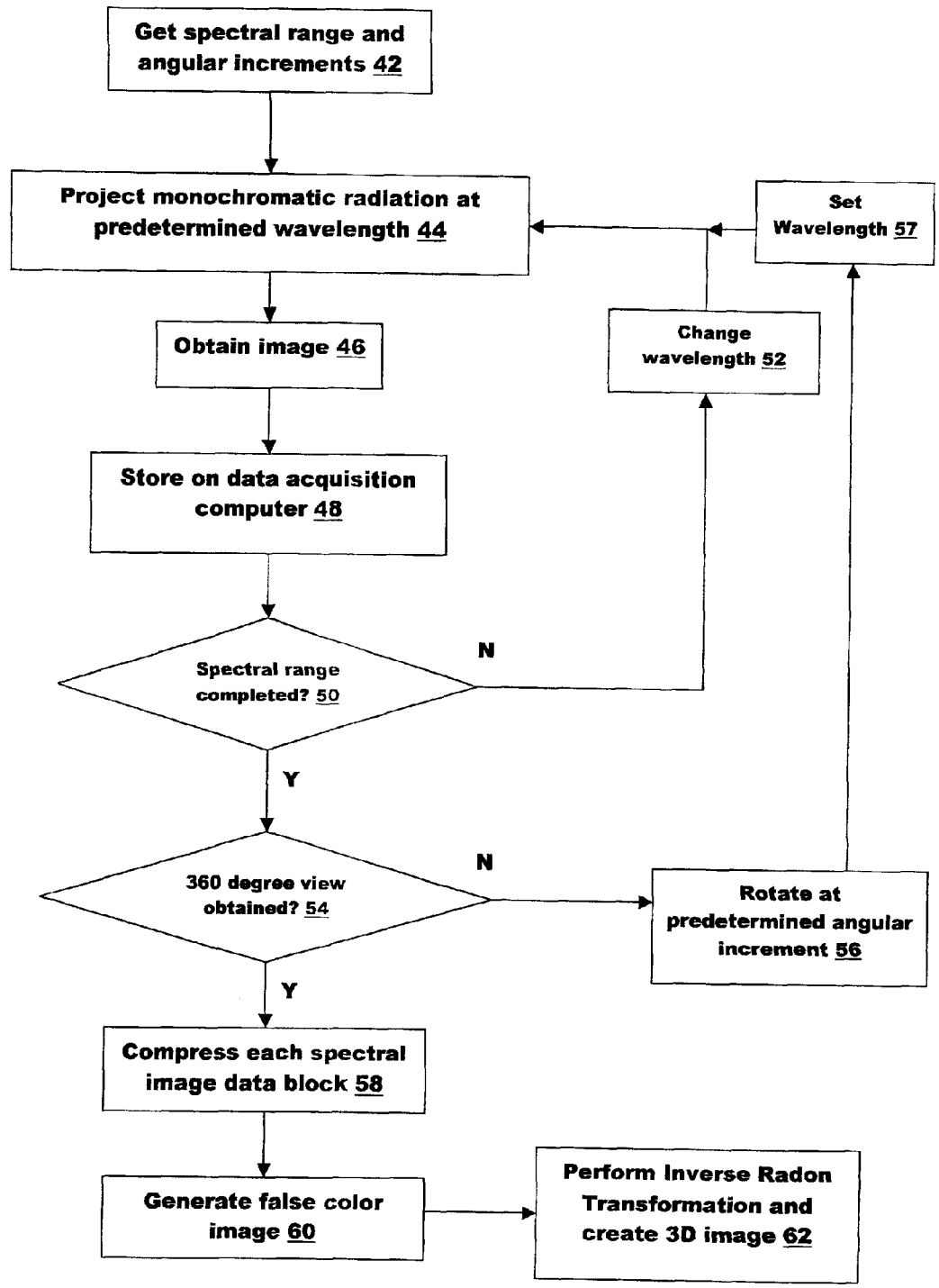
FIG. 7 is a flow chart for the process followed by a software program residing on the imaging system of FIG. 1.

FIG. 7 depicts an exemplary flow chart for the program residing on the instrument control computer 32 that controls the system components to obtain the spectral imaging information. The software object obtains the desired spectral image and angular increments (step 42) from a user or memory. A signal is sent to the monochrometer 12 via control line 26 to a predetermined wavelength of light onto the sample 20 for scanning (step 44). The projected radiation passes through the components of the system as previously mentioned and the control computer 32 sends a signal to the CCD detector 28 via control line 25 to capture the resulting image (step 46) and send it to the control computer 32 via a data channel 30. The program stores the image on the data acquisition computer 34 (step 48).

The object then queries whether the desired spectral range has been scanned (step 50). If it has not, the setting of the monochrometer is changed to the next wavelength of light (step 52) by sending the appropriate signal to the monochrometer via control line 26 and scans the object again (step 44–48). After the desired range is scanned, the software object queries whether the whole 360 degree view was obtained (step 54). If not, the sample is rotated (step 56) and the required images taken for the spectral range of that angular position (step 44–48).

Once the entire 360 degree view has been scanned, each spectral block is compressed (step 58) to generate the false color images (step 60). The false color images are then used to create the final 3D image by performing an inverse Radon transformation (step 62) with the source code of Tables 1 and 2.

The present invention may be used to image any objects through which near infrared radiation and/or mid-infrared radiation can pass. Desired information may be information about the density of living or nonliving biological tissue for detecting tumors or other malignant conditions or chemical spatial information of a pharmaceutical dose or microsphere throughout its three dimensional volume. By providing active ingredient mapping and water mapping in three dimensions, resulting images under the present invention show the position and identity of layers in a solid dosage form. The thickness of film coatings can be ascertained. In combination with related substance mapping, degradation occurring in a dosage form can be shown. Two dimensional imaging can be achieved for transdermal patches as well to find dosage concentration at specific positions to determine the distribution of the active components.

In the preceding specification, the invention has been described with reference to specific exemplary embodiments thereof. It will, however, be evident that various modifications and changes may be made thereto without departing from the broader spirit and scope of the invention as set forth in the claims that follow. The specification and drawings are accordingly to be regarded in an illustrative manner rather than a restrictive sense.

What is claimed is:

1. A three-dimensional spectral imaging system comprising:
   a source of collimated radiation disposed at a proximal side of an object; the collimated radiation having a predetermined wavelength;
   a scanning angle changer operatively connected to at least one of the radiation source and the object;
   a radiation detector disposed at a distal side of the object; and
   a processor coupled to the radiation detector, the processor receiving information from the radiation detector and generating a three dimensional spectral image of the object based upon a principal component analysis of the received information.

2. The imaging system of claim 1, wherein the source of collimated radiation includes a light source and a monochromer.

3. The imaging system of claim 2, wherein the source of collimated radiation further includes a collimator.

4. The imaging system of claim 3 wherein the collimator includes a polarizer.

5. The imaging system of claim 4, wherein the collimator further includes a quarter wave plate.

6. The imaging system of claim 3, wherein the collimator includes a set of baffles.

7. The imaging system of claim 3, wherein the collimator includes an array of fiber optic fibers.

8. A three-dimensional spectral imaging system comprising:
a source of collimated radiation disposed at a proximal side of an object, the collimated radiation having a predetermined wavelength;
a scanning angle changer operatively connected to at least one of the radiation source and the object;
a radiation detector disposed at a distal side of the object; and
a processor coupled to the radiation detector, the processor receiving information from the radiation detector and generating a three dimensional spectral image of a principal component of the received information.

9. The imaging system of claim 8, wherein the source of collimated radiation includes a light source and a monochromer.

10. The imaging system of claim 9, wherein the source of collimated radiation further includes a collimator.

11. The imaging system of claim 10 wherein the collimator includes a polarizer.

12. The imaging system of claim 10, wherein the collimator further includes a quarter wave plate.

13. The imaging system of claim 10, wherein the collimator includes a set of baffles.

14. The imaging system of claim 10, wherein the collimator includes an array of fiber optic fibers.

15. A three-dimensional spectral imaging system comprising:
a source of collimated radiation disposed at a proximal side of an object and including a light source and a monochromer, the collimated radiation having a predetermined wavelength between 1000 and 5000 nanometers;
a scanning angle changer operatively connected to at least one of the radiation source and the object;
a radiation detector disposed at a distal side of the object; and
a processor coupled to the radiation detector, the processor receiving information from the radiation detector and generating a three dimensional spectral image of the object.

16. The imaging system as recited in claim 15 further comprising an image display device for display of the three-dimensional image by the processor.

17. The imaging system of claim 15, wherein the source of collimated radiation further includes a collimator.

18. The imaging system of claim 17, wherein the collimator includes a polarizer.

19. The imaging system of claim 17, wherein the collimator further includes a quarter wave plate.

20. The imaging system of claim 17, wherein the collimator includes a set of baffles.

21. The imaging system of claim 17, wherein the collimator includes an array of fiber optic fibers.

22. A three-dimensional spectral imaging system for obtaining image information of a solid pharmaceutical dosage form, the system comprising:
a radiation source disposed at a proximal side of the dosage form for passing a radiation beam having a predetermined wavelength through the dosage form at a scanning angle;
a beam collimator disposed between the radiation source and the dosage form;
a scanning angle changer operatively connected to at least one of the radiation source and the dosage form;
a radiation detector disposed at a distal side of the dosage form for detecting a plurality of two-dimensional spectral images of the dosage form; and
a control computer for effecting operation of the radiation source, the radiation detector, and the scanning position changer, wherein the control computer enables the capturing the plurality of two-dimensional spectral images and is capable of determining a three-dimensional image of the dosage form using the plurality of two-dimensional spectral images.

23. The imaging system as recited in claim 22 further comprising an image display device for display of the three-dimensional image by the control computer.

24. The imaging system as recited in claim 22 wherein the beam collimator includes a focusing lens.

25. The imaging system as recited in claim 24 further comprising a first set of optical elements disposed between the focusing lens and the dosage form.

26. The imaging system as recited in claim 25 further comprising a second set of optical elements disposed between the dosage form and the radiation detector.

27. The imaging system as recited in claim 26 wherein the first and second set of optical elements each include a polarizer.

28. The imaging system as recited in claim 26 wherein the first and second set of optical elements each include a quarter-wave plate.

29. The imaging system as recited in claim 22 wherein the control computer includes a data storage device for storing the plurality of two-dimensional spectral images.

30. The imaging system as resited in claim 22 wherein the radiation source includes a lamp and a monochromer.

31. The imaging system as recited in claim 22 wherein the radiation beam is a near infrared radiation beam.

32. The imaging system as recited in claim 22 wherein the radiation beam is mid-infrared radiation beam.

33. The imaging system as recited in claim 22 wherein the radiation source includes a wavelength filter for causing the radiation beam to have the predetermined wavelength.

34. The imaging system as recited in claim 22 wherein the dosage form includes a microsphere.

35. The imaging system as recited in claim 34 further comprising an encapsulation material surrounding the microsphere.

36. A three-dimensional spectral imaging system for obtaining image information of an object, the system comprising:
a radiation source disposed at a proximal side of the object for passing a radiation beam having a predetermined wavelength through the object at a scanning angle;
a beam collimator disposed between the radiation source and the object;
a scanning angle changer operatively connected to at least one of the radiation source and the object, the scanning angle changer including a rotating stage;

a radiation detector disposed at a distal side of the object for detecting a plurality of two-dimensional spectral images of the object; and a control computer for effecting operation of the radiation source, the radiation detector, and the scanning position changer, wherein the control computer enables the capturing the plurality of two-dimensional spectral images and is capable of determining a three-dimensional image of the object using the plurality of two-dimensional spectral images.

37. The imaging system as recited in claim 36 wherein the scanning angle changer is capable of changing a position of the radiation source relative to the object.

38. The imaging system as recited in claim 36 wherein the object includes a biological tissue.

39. The imaging system as recited in claim 36 wherein the object includes a transdermal patch.

40. A three-dimensional spectral imaging system for obtaining image information of an object, the system comprising:

a radiation source disposed at a proximal side of the object for passing a radiation beam having a predetermined wavelength through the object at a scanning angle;

a beam collimator disposed between the radiation source and the object;

a scanning angle changer operatively connected to at least one of the radiation source and the object;

a radiation detector disposed at a distal side of the object for detecting a plurality of two-dimensional spectral images of the object;

a control computer for effecting operation of the radiation source, the radiation detector, and the scanning position changer, wherein the control computer enables the capturing the plurality of two-dimensional spectral images and is capable of determining a three-dimensional image of the object using the plurality of two-dimensional spectral images; and a plurality of radiation sources disposed in a circular relationship relative to the object, and wherein the scanning angle changer is capable of operating the radiation sources individually to change a respective scanning angle between each of the plurality of radiation sources and the object.

41. The imaging system as recited in claim 40 wherein the radiation detector includes a CCD detector.

42. The imaging system as recited in claim 41 wherein the CCD detector includes a focal plane array camera.

43. The imaging system as recited in claim 42 wherein the focal plane array camera is an indium antimony liquid nitrogen cooled focal plane array camera.

44. The imaging system as recited in claim 40 further comprising software executable by the control computer, the software written in a programming language having a numeric computing environment to perform the determining of the three-dimensional image.

45. A three-dimensional spectral imaging system for obtaining image information of an object, the system comprising:

a radiation source disposed at a proximal side of the object for passing a radiation beam having a predetermined wavelength through the object at a scanning angle;

a beam collimator disposed between the radiation source and the object;

a scanning angle changer operatively connected to at least one of the radiation source and the object;

a radiation detector disposed at a distal side of the object for detecting a plurality of two-dimensional spectral images of the object; and a control computer for effecting operation of the radiation source, the radiation detector, and the scanning position changer, wherein the control computer enables the capturing the plurality of two-dimensional spectral images and is capable of determining a three-dimensional image of the object using the plurality of two-dimensional spectral images;

wherein the control computer is capable of effecting operation of the radiation source, the radiation detector, and the scanning angle changer so as to change the predetermined wavelength of the radiation beam and the scanning angle changer and wherein each of the plurality of two-dimensional spectral images has a respective scanning angle and a respective wavelength.

46. The imaging system as recited in claim 45 wherein the control computer is capable of determining a spectral image data block by capturing at least two two-dimensional spectral images at a same respective predetermined scanning angle and a different respective predetermined wavelength.

47. The imaging system as recited in claim 46 wherein the control computer is capable of compressing the spectral image data block.

48. The imaging system as recited in claim 46 wherein the control computer is capable of capturing the two-dimensional spectral images at a plurality of respective predetermined scanning angles so as to provide a 360 degree view of the object and so as to determine a plurality of respective spectral image data blocks.

49. The imaging system as recited in claim 48 wherein the control computer is capable of generating a respective RGB false color image from each of the plurality of respective spectral image data blocks.

50. The imaging system as recited in claim 49 wherein the control computer is capable of combining the generated RGB false color images to create a three-dimensional volume visualization package.

51. The imaging system as recited in claim 50 wherein the control computer is capable of determining the three-dimensional image of the object using the three-dimensional volume visualization package.

52. A method for three-dimensional imaging of an object comprising the steps of:

directing a radiation beam having a predetermined wavelength from a radiation source through the object at a predetermined scanning angle;

collimating the radiation beam;

changing the predetermined wavelength;

changing the predetermined scanning angle;

capturing a plurality of two-dimensional spectral images of the object, each of the plurality of two-dimensional spectral images being captured at a respective scanning angle and a respective predetermined wavelength; and reconstructing a three-dimensional image of the object using the plurality of two-dimensional spectral images.

53. The method as recited in claim 52 wherein the capturing is performed so as to capture at least two two-dimensional spectral images at a same respective predetermined scanning angle and at different respective predetermined wavelengths.

54. The method as recited in claim 53 wherein the capturing of the at least two two-dimensional spectral images at a same respective predetermined scanning angle and at different respective predetermined wavelengths is performed so as to determine a spectral image data block.

55. The method as recited in claim 54 further comprising compressing the spectral image data block.

56. The method as recited in claim 55 wherein the compressing of the spectral image data block includes compressing using Principal Component Analysis.

57. The method as recited in claim 54 wherein the capturing is performed at a plurality of respective predetermined scanning angles so as to provide a 360 degree view of the object and so as to determine a plurality of respective spectral image data blocks.

58. The method as recited in claim 57 further comprising generating a respective RGB false color image from each of the plurality of respective spectral image data blocks.

59. The method as recited in claim 58 further comprising combining the generated RGB false color images to create a three-dimensional volume visualization package.

60. The method as recited in claim 59 wherein the reconstruction step is performed using the three-dimensional volume visualization package.

61. The method as recited in claim 59 wherein the combining of the RGB images includes creating the three-dimensional visualization package using the inverse Radon transformation.

62. The method as recited in claim 52 wherein the capturing is performed so as to capture a plurality of two-dimensional spectral images at a same respective predetermined wavelength and at different respective predetermined scanning angles.

63. The method as recited in claim 52 wherein the changing of the scanning angle includes changing a relative position of one of the object and the radiation source.

64. The method as recited in claim 63 wherein the changing of the relative position includes rotating the object.

65. The method as recited in claim 63 wherein the changing of the relative position includes moving the radiation source in a circular trajectory.

66. The method as recited in claim 63 wherein the changing of the relative position includes positioning a plurality of near infrared radiation sources in a circular trajectory around the object and activating each of the plurality of sources in adjacent succession.

67. The method as recited in claim 52 further comprising combining the plurality of two-dimensional spectral images to obtain image reconstruction data and wherein the reconstructing includes using the image reconstruction data.

68. The method as recited in claim 52 wherein the capturing is performed by detecting a portion of the radiation beam that has not been scattered after having passed through the object.

69. The method as recited in claim 52 further comprising storing the plurality of spectral images on a storage device.

70. The method as recited in claim 52 wherein the reconstructing is performed by using a control computer.

71. The method as recited in claim 70 wherein the directing of the radiation beam, the changing of the predetermined wavelength, the changing of the scanning angle, and the capturing of the plurality of two-dimensional spectral images are performed using the control computer according to a prescribed sequence.

72. The method as recited in claim 52 further comprising displaying the three-dimensional image of the object on an image display.

73. The method as recited in claim 52 further comprising determining the predetermined wavelengths.

74. The method as recited in claim 52 further comprising filtering the radiation beam to project a monochromatic radiation beam from the radiation source onto the object.

75. The method as recited in claim 52 wherein the directing of the radiation beam includes passing the radiation through a first set of optical elements.

76. The method as recited in claim 75 wherein passing the radiation through a first set of optical elements further includes passing the radiation through a polarizer and a retardation plate.

77. The method as recited in claim 76 wherein passing the radiation through a polarizer and a retardation plate further comprises passing the radiation through a quarter-wave retardation plate.

78. The method as recited in claim 52 wherein the directing of the radiation beam includes passing the radiation beam through a second set of optical elements.

79. The method as recited in claim 78 wherein passing the radiation beam through a second set of optical elements includes passing the radiation through a polarizer.

80. The method as recited in claim 79 wherein passing the radiation through a second set of optical elements includes passing the radiation through a retardation plate.

81. The method as recited in claim 80 wherein passing the radiation through a retardation plate includes passing the radiation through a quarter-wave plate.

82. The method as recited in claim 52 wherein the capturing includes capturing the plurality of two-dimensional spectral images using a CCD detector.

83. The method as recited in claim 82 wherein capturing the spectral images using a CCD detector includes capturing the spectral images on a focal plane array camera.

84. The method as recited in claim 83 wherein capturing the spectral images on a focal plane array camera includes capturing the spectral images on an indium antimony liquid nitrogen cooled focal plane array camera.

85. The method as recited in claim 52 wherein the object is a pharmaceutical dose.

86. The method as recited in claim 52 wherein the object is a biological tissue.

87. The method as recited in claim 52 wherein the object is a transdermal patch.

88. The method as recited in claim 52 wherein the reconstructing is performed using software written in a language having a numeric computing environment.

89. The method as recited in claim 52 wherein the object includes a microsphere.

90. The method as recited in claim 89 further comprising an encapsulation material surrounding the microsphere.

* * * * *